(12) United States Patent
Arts et al.

(10) Patent No.: US 7,972,332 B2
(45) Date of Patent: *Jul. 5, 2011

(54) SYSTEM AND METHOD FOR CONTROLLING ELECTROSURGICAL SNARES

(75) Inventors: Gene H. Arts, Berthoud, CO (US); Jason L. Craig, Loveland, CO (US); Dale F. Schmaltz, Fort Collins, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/639,243

(22) Filed: Dec. 16, 2009

(65) Prior Publication Data

US 2010/0094285 A1   Apr. 15, 2010

Related U.S. Application Data

(63) Continuation of application No. 11/367,723, filed on Mar. 3, 2006, now Pat. No. 7,651,493.

(51) Int. Cl.
*A61B 18/14* (2006.01)
(52) U.S. Cl. .......................... 606/47; 606/41
(58) Field of Classification Search ............... 606/32–50
See application file for complete search history.

(56) References Cited

U.S. PATENT DOCUMENTS

| | | |
|---|---|---|
| 1,787,709 A | 1/1931 | Wappler |
| 1,813,902 A | 7/1931 | Bovie |
| 1,841,968 A | 1/1932 | Lowry |
| 1,863,118 A | 6/1932 | Liebel |
| 1,945,867 A | 2/1934 | Rawls |
| 2,827,056 A | 3/1958 | Degelman |
| 2,849,611 A | 8/1958 | Adams |
| 3,058,470 A | 10/1962 | Seeliger et al. |
| 3,089,496 A | 5/1963 | Degelman |
| 3,154,365 A | 10/1964 | Crimmins |
| 3,163,165 A | 12/1964 | Islikawa |
| 3,252,052 A | 5/1966 | Nash |
| 3,391,351 A | 7/1968 | Trent |
| 3,413,480 A | 11/1968 | Biard et al. |

(Continued)

FOREIGN PATENT DOCUMENTS

DE    179607    3/1905

(Continued)

OTHER PUBLICATIONS

U.S. Appl. No. 10/406,690, filed Apr. 3, 2003.

(Continued)

*Primary Examiner* — Michael Peffley
*Assistant Examiner* — Ronald Hupczey, Jr.

(57) ABSTRACT

A system and method for controlling electrosurgical snares are disclosed. The system includes an electrosurgical instrument having an elongate tubular sheath having proximal and distal ends, the sheath having a longitudinal axis defined therethrough and a shaft having proximal and distal ends. The shaft extends through and is axially movable relative to the sheath. A snare loop is provided at the distal end of the shaft and is configured for encircling tissue. Movement of the shaft relative to the tubular sheath changes the diameter of the exposed snare loop. A feedback sensor operatively connected to the elongated tubular sheath which determines at least one condition of the snare loop, and an electrosurgical generator provides electrosurgical energy to the electrosurgical snare instrument. The generator is configured to receive feedback measurements from the electrosurgical snare instrument and to adjust electrosurgical energy as a function of the measurements.

19 Claims, 6 Drawing Sheets

U.S. PATENT DOCUMENTS

| | | |
|---|---|---|
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Bierlein |
| 3,743,918 A | 7/1973 | Maitre |
| 3,766,434 A | 10/1973 | Sherman |
| 3,768,019 A | 10/1973 | Podowski |
| 3,768,482 A | 10/1973 | Shaw |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,898,554 A | 8/1975 | Knudsen |
| 3,905,373 A | 9/1975 | Gonser |
| 3,908,176 A | 9/1975 | De Boer et al. |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 4,005,714 A | 2/1977 | Hilebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gonser |
| 4,209,018 A | 6/1980 | Meinke et al. |
| 4,229,714 A | 10/1980 | Yu |
| 4,231,372 A | 11/1980 | Newton |
| 4,232,676 A | 11/1980 | Herczog |
| 4,237,887 A | 12/1980 | Gonser |
| 4,281,373 A | 7/1981 | Mabille |
| 4,287,557 A | 9/1981 | Brehse |
| 4,296,413 A | 10/1981 | Milkovic |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,436,091 A | 3/1984 | Banko |
| 4,437,464 A | 3/1984 | Crow |
| 4,438,766 A | 3/1984 | Bowers |
| 4,463,759 A | 8/1984 | Garito et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,532,924 A | 8/1985 | Auth et al. |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,572,190 A | 2/1986 | Azam et al. |
| 4,582,057 A | 4/1986 | Auth et al. |
| 4,586,120 A | 4/1986 | Malik et al. |
| 4,590,934 A | 5/1986 | Malis et al. |
| 4,595,248 A | 6/1986 | Brown |
| 4,608,977 A | 9/1986 | Brown |
| 4,615,330 A | 10/1986 | Nagasaki et al. |
| 4,630,218 A | 12/1986 | Hurley |
| 4,632,109 A | 12/1986 | Patterson |
| 4,644,955 A | 2/1987 | Mioduski |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,691,703 A | 9/1987 | Auth et al. |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,754,757 A | 7/1988 | Feucht |
| 4,767,999 A | 8/1988 | VerPlanck |
| 4,768,969 A | 9/1988 | Bauer et al. |
| 4,785,829 A | 11/1988 | Convert et al. |
| 4,788,634 A | 11/1988 | Schlecht et al. |
| 4,805,621 A | 2/1989 | Heinze et al. |
| 4,818,954 A | 4/1989 | Flachenecker et al. |
| 4,827,927 A | 5/1989 | Newton |
| 4,848,335 A | 7/1989 | Manes |
| 4,860,745 A | 8/1989 | Farin et al. |
| 4,862,889 A | 9/1989 | Feucht |
| 4,887,199 A | 12/1989 | Whittle |
| 4,890,610 A | 1/1990 | Kirwan et al. |
| 4,903,696 A | 2/1990 | Stasz et al. |
| 4,907,589 A | 3/1990 | Cosman |
| 4,922,210 A | 5/1990 | Flachenecker et al. |
| 4,925,089 A | 5/1990 | Chaparro et al. |
| 4,931,047 A | 6/1990 | Broadwin et al. |
| 4,931,717 A | 6/1990 | Gray et al. |
| 4,938,761 A | 7/1990 | Ensslin |
| 4,942,313 A | 7/1990 | Kinzel |

| | | | | | |
|---|---|---|---|---|---|
| 4,959,606 A | 9/1990 | Forge | 5,422,567 A | 6/1995 | Matsunaga |
| 4,961,047 A | 10/1990 | Carder | 5,422,926 A | 6/1995 | Smith et al. |
| 4,961,435 A | 10/1990 | Kitagawa et al. | 5,423,808 A | 6/1995 | Edwards et al. |
| 4,966,597 A | 10/1990 | Cosman | 5,423,809 A | 6/1995 | Klicek |
| 4,969,885 A | 11/1990 | Farin | 5,423,810 A | 6/1995 | Goble et al. |
| 4,992,719 A | 2/1991 | Harvey | 5,423,811 A | 6/1995 | Imran et al. |
| 4,993,430 A | 2/1991 | Shimoyama et al. | 5,425,704 A | 6/1995 | Sakurai et al. |
| 4,995,877 A | 2/1991 | Ams et al. | 5,429,596 A | 7/1995 | Arias et al. |
| 5,015,227 A | 5/1991 | Broadwin et al. | 5,430,434 A | 7/1995 | Lederer et al. |
| 5,024,668 A | 6/1991 | Peters et al. | 5,432,459 A | 7/1995 | Thompson |
| 5,044,977 A | 9/1991 | Vindigni | 5,433,739 A | 7/1995 | Sluijter et al. |
| 5,067,953 A | 11/1991 | Feucht | 5,436,566 A | 7/1995 | Thompson |
| 5,075,839 A | 12/1991 | Fisher et al. | 5,438,302 A | 8/1995 | Goble |
| 5,087,257 A | 2/1992 | Farin | 5,443,463 A | 8/1995 | Stern et al. |
| 5,099,840 A | 3/1992 | Goble et al. | 5,445,635 A | 8/1995 | Denen |
| 5,103,804 A | 4/1992 | Abele et al. | 5,451,224 A | 9/1995 | Goble et al. |
| 5,108,389 A | 4/1992 | Cosmescu | 5,452,725 A | 9/1995 | Martenson |
| 5,108,391 A | 4/1992 | Flachenecker | 5,454,809 A | 10/1995 | Janssen |
| 5,119,284 A | 6/1992 | Fisher et al. | 5,458,597 A | 10/1995 | Edwards et al. |
| 5,122,137 A | 6/1992 | Lennox | 5,462,521 A | 10/1995 | Brucker et al. |
| 5,133,711 A | 7/1992 | Hagen | 5,472,441 A | 12/1995 | Edwards et al. |
| 5,151,102 A | 9/1992 | Kamiyama et al. | 5,472,443 A | 12/1995 | Cordis et al. |
| 5,152,762 A | 10/1992 | McElhenney | 5,474,464 A | 12/1995 | Drewnicki |
| 5,157,603 A | 10/1992 | Scheller et al. | 5,480,399 A | 1/1996 | Hebborn |
| 5,160,334 A | 11/1992 | Billings et al. | 5,483,952 A | 1/1996 | Aranyi |
| 5,161,893 A | 11/1992 | Shigezawa et al. | 5,496,312 A | 3/1996 | Klicek |
| 5,167,658 A | 12/1992 | Ensslin | 5,496,313 A | 3/1996 | Gentelia et al. |
| 5,167,659 A | 12/1992 | Ohtomo et al. | 5,496,314 A | 3/1996 | Eggers |
| 5,190,517 A | 3/1993 | Zieve et al. | 5,500,012 A | 3/1996 | Brucker et al. |
| 5,196,008 A | 3/1993 | Kuenecke | 5,500,616 A | 3/1996 | Ochi |
| 5,196,009 A | 3/1993 | Kirwan, Jr. | 5,511,993 A | 4/1996 | Yamada et al. |
| 5,201,900 A | 4/1993 | Nardella | 5,514,129 A | 5/1996 | Smith |
| 5,207,691 A | 5/1993 | Nardella | 5,520,684 A | 5/1996 | Imran |
| 5,230,623 A | 7/1993 | Guthrie et al. | 5,531,774 A | 7/1996 | Schulman et al. |
| 5,233,515 A | 8/1993 | Cosman | 5,534,018 A | 7/1996 | Wahlstrand et al. |
| 5,234,427 A | 8/1993 | Ohtomo et al. | 5,536,267 A | 7/1996 | Edwards et al. |
| 5,249,121 A | 9/1993 | Baum et al. | 5,540,677 A | 7/1996 | Sinofsky |
| 5,249,585 A | 10/1993 | Turner et al. | 5,540,681 A | 7/1996 | Strul et al. |
| 5,254,117 A | 10/1993 | Rigby et al. | 5,540,682 A | 7/1996 | Gardner et al. |
| RE34,432 E | 11/1993 | Bertrand | 5,540,683 A | 7/1996 | Ichikawa |
| 5,267,994 A | 12/1993 | Gentelia et al. | 5,540,684 A | 7/1996 | Hassler, Jr. |
| 5,267,997 A | 12/1993 | Farin | 5,541,376 A | 7/1996 | Ladtkow et al. |
| 5,281,213 A | 1/1994 | Milder et al. | 5,545,161 A | 8/1996 | Imran |
| 5,282,840 A | 2/1994 | Hudrlik | 5,556,396 A | 9/1996 | Cohen et al. |
| 5,290,283 A | 3/1994 | Suda | 5,558,671 A | 9/1996 | Yates |
| 5,295,857 A | 3/1994 | Toly | 5,562,720 A | 10/1996 | Stern et al. |
| 5,300,068 A | 4/1994 | Rosar et al. | 5,569,242 A | 10/1996 | Lax et al. |
| 5,300,070 A | 4/1994 | Gentelia | 5,571,147 A | 11/1996 | Sluijter et al. |
| 5,304,917 A | 4/1994 | Somerville | 5,573,533 A | 11/1996 | Strul |
| 5,318,563 A | 6/1994 | Malis et al. | 5,584,830 A | 12/1996 | Ladd et al. |
| 5,323,778 A | 6/1994 | Kandarpa et al. | 5,588,432 A | 12/1996 | Crowley |
| 5,324,283 A | 6/1994 | Heckele | 5,596,466 A | 1/1997 | Ochi |
| 5,330,518 A | 7/1994 | Neilson et al. | 5,599,344 A | 2/1997 | Paterson |
| 5,334,183 A | 8/1994 | Wuchinich | 5,599,345 A | 2/1997 | Edwards et al. |
| 5,334,193 A | 8/1994 | Nardella | 5,599,348 A | 2/1997 | Gentelia et al. |
| 5,341,807 A | 8/1994 | Nardella | 5,605,150 A | 2/1997 | Radons et al. |
| 5,342,356 A | 8/1994 | Ellman | 5,609,560 A | 3/1997 | Ichikawa et al. |
| 5,342,357 A | 8/1994 | Nardella | 5,613,966 A | 3/1997 | Makower et al. |
| 5,342,409 A | 8/1994 | Mullett | 5,620,481 A | 4/1997 | Desai et al. |
| 5,346,406 A | 9/1994 | Hoffman et al. | 5,626,575 A | 5/1997 | Crenner |
| 5,346,491 A | 9/1994 | Oertli | 5,628,745 A | 5/1997 | Bek |
| 5,348,554 A | 9/1994 | Imran et al. | 5,628,771 A | 5/1997 | Mizukawa et al. |
| 5,369,567 A | 11/1994 | Furuta et al. | 5,643,330 A | 7/1997 | Holsheimer et al. |
| 5,370,645 A | 12/1994 | Klicek et al. | 5,647,869 A | 7/1997 | Goble et al. |
| 5,370,672 A | 12/1994 | Fowler et al. | 5,647,871 A | 7/1997 | Levine et al. |
| 5,370,675 A | 12/1994 | Edwards et al. | 5,651,780 A | 7/1997 | Jackson et al. |
| 5,372,596 A | 12/1994 | Klicek et al. | 5,658,322 A | 8/1997 | Fleming |
| 5,383,874 A | 1/1995 | Jackson | 5,660,567 A | 8/1997 | Nierlich et al. |
| 5,383,876 A | 1/1995 | Nardella | 5,664,953 A | 9/1997 | Reylek |
| 5,383,917 A | 1/1995 | Desai et al. | 5,674,217 A | 10/1997 | Wahlstrom et al. |
| 5,385,148 A | 1/1995 | Lesh et al. | 5,678,568 A | 10/1997 | Uchikubo et al. |
| 5,400,267 A | 3/1995 | Denen et al. | 5,681,307 A | 10/1997 | McMahan |
| 5,403,311 A | 4/1995 | Abele et al. | 5,685,840 A | 11/1997 | Schechter et al. |
| 5,403,312 A | 4/1995 | Yates et al. | 5,688,267 A | 11/1997 | Panescu et al. |
| 5,409,000 A | 4/1995 | Imran | 5,693,042 A | 12/1997 | Boiarski et al. |
| 5,409,485 A | 4/1995 | Suda | 5,693,078 A | 12/1997 | Desai et al. |
| 5,413,573 A | 5/1995 | Koivukangas | 5,694,304 A | 12/1997 | Telefus et al. |
| 5,414,238 A | 5/1995 | Steigerwald et al. | 5,695,494 A | 12/1997 | Becker |
| 5,417,719 A | 5/1995 | Hull et al. | 5,696,441 A | 12/1997 | Mak et al. |

| | | | | | | |
|---|---|---|---|---|---|---|
| 5,697,925 A | 12/1997 | Taylor | | 6,017,338 A | 1/2000 | Brucker et al. |
| 5,697,927 A | 12/1997 | Imran et al. | | 6,017,354 A | 1/2000 | Culp et al. |
| 5,702,386 A | 12/1997 | Stern et al. | | 6,022,346 A | 2/2000 | Panescu et al. |
| 5,702,429 A | 12/1997 | King | | 6,022,347 A | 2/2000 | Lindenmeier et al. |
| 5,707,369 A | 1/1998 | Vaitekunas et al. | | 6,033,399 A | 3/2000 | Gines |
| 5,712,772 A | 1/1998 | Telefus et al. | | 6,039,731 A | 3/2000 | Taylor et al. |
| 5,713,896 A | 2/1998 | Nardella | | 6,039,732 A | 3/2000 | Ichikawa et al. |
| 5,718,246 A | 2/1998 | Vona | | 6,041,260 A | 3/2000 | Stern et al. |
| 5,720,742 A | 2/1998 | Zacharias | | 6,044,283 A | 3/2000 | Fein et al. |
| 5,720,744 A | 2/1998 | Eggleston et al. | | 6,053,910 A | 4/2000 | Fleenor |
| 5,722,975 A | 3/1998 | Edwards et al. | | 6,053,912 A | 4/2000 | Panescu et al. |
| 5,729,448 A | 3/1998 | Haynie et al. | | 6,055,458 A | 4/2000 | Cochran et al. |
| 5,733,281 A | 3/1998 | Nardella | | 6,056,745 A | 5/2000 | Panescu et al. |
| 5,735,846 A | 4/1998 | Panescu et al. | | 6,056,746 A | 5/2000 | Goble et al. |
| 5,738,683 A * | 4/1998 | Osypka .......................... 606/47 | | 6,059,781 A | 5/2000 | Yamanashi et al. |
| 5,743,900 A | 4/1998 | Hara | | 6,063,075 A | 5/2000 | Mihori |
| 5,743,903 A | 4/1998 | Stern et al. | | 6,063,078 A | 5/2000 | Wittkampf |
| 5,749,869 A | 5/1998 | Lindenmeier et al. | | 6,066,137 A | 5/2000 | Greep |
| 5,749,871 A | 5/1998 | Hood et al. | | 6,068,627 A | 5/2000 | Orszulak et al. |
| 5,755,715 A | 5/1998 | Stern | | 6,074,089 A | 6/2000 | Hollander et al. |
| 5,762,609 A | 6/1998 | Benaron et al. | | 6,074,386 A | 6/2000 | Goble et al. |
| 5,766,153 A | 6/1998 | Eggers et al. | | 6,074,388 A | 6/2000 | Tockweiler et al. |
| 5,766,165 A | 6/1998 | Gentelia et al. | | 6,080,149 A | 6/2000 | Huang et al. |
| 5,769,847 A | 6/1998 | Panescu | | 6,088,614 A | 7/2000 | Swanson |
| 5,772,659 A | 6/1998 | Becker et al. | | 6,090,123 A | 7/2000 | Culp et al. |
| 5,788,688 A | 8/1998 | Bauer et al. | | 6,093,186 A | 7/2000 | Goble |
| 5,792,138 A | 8/1998 | Shipp | | 6,102,497 A | 8/2000 | Ehr et al. |
| 5,797,902 A | 8/1998 | Netherly | | 6,102,907 A | 8/2000 | Smethers et al. |
| 5,807,253 A | 9/1998 | Dumoulin et al. | | 6,106,524 A | 8/2000 | Eggers et al. |
| 5,810,804 A | 9/1998 | Gough et al. | | 6,113,591 A | 9/2000 | Whayne et al. |
| 5,814,092 A | 9/1998 | King | | 6,113,592 A | 9/2000 | Taylor |
| 5,817,091 A | 10/1998 | Nardella et al. | | 6,113,593 A | 9/2000 | Tu et al. |
| 5,817,093 A | 10/1998 | Williamson, IV et al. | | 6,113,596 A | 9/2000 | Hooven |
| 5,820,568 A | 10/1998 | Willis | | 6,123,701 A | 9/2000 | Nezhat |
| 5,827,271 A | 10/1998 | Bussey et al. | | 6,123,702 A | 9/2000 | Swanson et al. |
| 5,830,212 A | 11/1998 | Cartmell | | 6,132,429 A | 10/2000 | Baker |
| 5,836,909 A | 11/1998 | Cosmescu | | 6,142,992 A | 11/2000 | Cheng et al. |
| 5,836,943 A | 11/1998 | Miller, III | | 6,155,975 A | 12/2000 | Urich et al. |
| 5,836,990 A | 11/1998 | Li | | 6,162,184 A | 12/2000 | Swanson et al. |
| 5,843,019 A | 12/1998 | Eggers et al. | | 6,162,217 A | 12/2000 | Kannenberg et al. |
| 5,843,075 A | 12/1998 | Taylor | | 6,165,169 A | 12/2000 | Panescu et al. |
| 5,846,236 A | 12/1998 | Lindenmeier et al. | | 6,171,304 B1 | 1/2001 | Netherly et al. |
| 5,849,010 A | 12/1998 | Wurzer et al. | | 6,183,468 B1 | 2/2001 | Swanson et al. |
| 5,853,409 A | 12/1998 | Swanson et al. | | 6,186,147 B1 | 2/2001 | Cobb |
| 5,860,832 A | 1/1999 | Wayt et al. | | 6,188,211 B1 | 2/2001 | Rincon-Mora et al. |
| 5,865,788 A | 2/1999 | Edwards et al. | | 6,193,713 B1 | 2/2001 | Geistert et al. |
| 5,868,737 A | 2/1999 | Taylor et al. | | 6,197,023 B1 | 3/2001 | Muntermann |
| 5,868,739 A | 2/1999 | Lindenmeier et al. | | 6,203,541 B1 | 3/2001 | Keppel |
| 5,868,740 A | 2/1999 | LeVeen et al. | | 6,210,403 B1 | 4/2001 | Klicek |
| 5,871,481 A | 2/1999 | Kannenberg et al. | | 6,216,704 B1 | 4/2001 | Ingle et al. |
| 5,891,142 A | 4/1999 | Eggers et al. | | 6,222,356 B1 | 4/2001 | Taghizadeh-Kaschani |
| 5,893,848 A | 4/1999 | Negus et al. | | 6,228,078 B1 | 5/2001 | Eggers et al. |
| 5,897,552 A | 4/1999 | Edwards et al. | | 6,228,080 B1 | 5/2001 | Gines |
| 5,906,614 A | 5/1999 | Stern et al. | | 6,228,081 B1 | 5/2001 | Goble |
| 5,908,444 A | 6/1999 | Azure | | 6,231,569 B1 | 5/2001 | Bek |
| 5,913,882 A | 6/1999 | King | | 6,232,556 B1 | 5/2001 | Daugherty et al. |
| 5,921,982 A | 7/1999 | Lesh et al. | | 6,235,020 B1 | 5/2001 | Cheng et al. |
| 5,925,070 A | 7/1999 | King et al. | | 6,235,022 B1 | 5/2001 | Hallock et al. |
| 5,931,836 A | 8/1999 | Hatta et al. | | 6,237,604 B1 | 5/2001 | Burnside et al. |
| 5,938,690 A | 8/1999 | Law et al. | | 6,238,387 B1 | 5/2001 | Miller, III |
| 5,944,553 A | 8/1999 | Yasui et al. | | 6,238,388 B1 | 5/2001 | Ellman |
| 5,948,007 A | 9/1999 | Starkebaum et al. | | 6,241,723 B1 | 6/2001 | Heim et al. |
| 5,951,545 A | 9/1999 | Schilling | | 6,241,725 B1 | 6/2001 | Cosman |
| 5,951,546 A | 9/1999 | Lorentzen | | 6,243,654 B1 | 6/2001 | Johnson et al. |
| 5,954,686 A | 9/1999 | Garito et al. | | 6,245,061 B1 | 6/2001 | Panescu et al. |
| 5,954,717 A | 9/1999 | Behl et al. | | 6,245,063 B1 | 6/2001 | Uphoff |
| 5,954,719 A | 9/1999 | Chen et al. | | 6,245,065 B1 | 6/2001 | Panescu |
| 5,957,961 A | 9/1999 | Maguire et al. | | 6,246,912 B1 | 6/2001 | Sluijter et al. |
| 5,959,253 A | 9/1999 | Shinchi | | 6,251,106 B1 | 6/2001 | Becker et al. |
| 5,961,344 A | 10/1999 | Rosales et al. | | 6,254,422 B1 | 7/2001 | Feye-Hohmann |
| 5,964,746 A | 10/1999 | McCary | | 6,258,085 B1 | 7/2001 | Eggleston |
| 5,971,980 A | 10/1999 | Sherman | | 6,261,285 B1 | 7/2001 | Novak |
| 5,971,981 A | 10/1999 | Hill et al. | | 6,261,286 B1 | 7/2001 | Goble et al. |
| 5,976,128 A | 11/1999 | Schilling et al. | | 6,267,760 B1 | 7/2001 | Swanson |
| 5,983,141 A | 11/1999 | Sluijter et al. | | 6,273,886 B1 | 8/2001 | Edwards |
| 6,007,532 A | 12/1999 | Netherly | | 6,275,786 B1 | 8/2001 | Daners |
| 6,010,499 A | 1/2000 | Cobb | | 6,293,941 B1 | 9/2001 | Strul |
| 6,013,074 A | 1/2000 | Taylor | | 6,293,942 B1 | 9/2001 | Goble et al. |
| 6,014,581 A | 1/2000 | Whayne et al. | | 6,293,943 B1 | 9/2001 | Panescu et al. |

| | | | | | | |
|---|---|---|---|---|---|---|
| 6,296,636 B1 | 10/2001 | Cheng et al. | | 6,651,669 B1 | 11/2003 | Burnside |
| 6,306,131 B1 | 10/2001 | Hareyama et al. | | 6,652,513 B2 | 11/2003 | Panescu et al. |
| 6,306,134 B1 | 10/2001 | Goble et al. | | 6,652,514 B2 | 11/2003 | Ellman |
| 6,309,386 B1 | 10/2001 | Bek | | 6,653,569 B1 | 11/2003 | Sung |
| 6,322,558 B1 | 11/2001 | Taylor et al. | | 6,656,177 B2 | 12/2003 | Truckai et al. |
| 6,325,799 B1 | 12/2001 | Goble | | 6,663,623 B1 | 12/2003 | Oyama et al. |
| 6,329,778 B1 | 12/2001 | Culp et al. | | 6,663,624 B2 | 12/2003 | Edwards et al. |
| 6,337,998 B1 | 1/2002 | Behl et al. | | 6,663,627 B2 | 12/2003 | Francischelli et al. |
| 6,338,657 B1 | 1/2002 | Harper et al. | | 6,666,860 B1 | 12/2003 | Takahashi |
| 6,350,262 B1 | 2/2002 | Ashley | | 6,672,151 B1 | 1/2004 | Schultz et al. |
| 6,358,245 B1 | 3/2002 | Edwards | | 6,679,875 B2 | 1/2004 | Honda |
| 6,364,877 B1 | 4/2002 | Goble et al. | | 6,682,527 B2 | 1/2004 | Strul |
| 6,370,408 B1 | 4/2002 | Merchant et al. | | 6,685,700 B2 | 2/2004 | Behl |
| 6,371,963 B1 * | 4/2002 | Nishtala et al. ............... 606/113 | | 6,685,701 B2 | 2/2004 | Orszulak et al. |
| 6,383,183 B1 | 5/2002 | Sekino et al. | | 6,685,703 B2 | 2/2004 | Pearson et al. |
| 6,391,024 B1 | 5/2002 | Sun et al. | | 6,689,131 B2 | 2/2004 | McClurken |
| 6,398,779 B1 | 6/2002 | Buysse et al. | | 6,692,489 B1 | 2/2004 | Heim |
| 6,398,781 B1 | 6/2002 | Goble et al. | | 6,693,782 B1 | 2/2004 | Lash |
| 6,402,741 B1 | 6/2002 | Keppel et al. | | 6,695,837 B2 | 2/2004 | Howell |
| 6,402,742 B1 | 6/2002 | Blewett et al. | | 6,696,844 B2 | 2/2004 | Taylor et al. |
| 6,402,743 B1 | 6/2002 | Orszulak et al. | | 6,712,813 B2 | 3/2004 | Ellman |
| 6,402,748 B1 | 6/2002 | Schoenman et al. | | 6,730,078 B2 | 5/2004 | Simpson et al. |
| 6,409,722 B1 | 6/2002 | Hoey et al. | | 6,730,079 B2 | 5/2004 | Lovewell |
| 6,413,256 B1 | 7/2002 | Truckai et al. | | 6,730,080 B2 | 5/2004 | Harano |
| 6,416,509 B1 | 7/2002 | Goble et al. | | 6,733,495 B1 | 5/2004 | Bek |
| 6,422,896 B2 | 7/2002 | Aoki et al. | | 6,733,498 B2 | 5/2004 | Paton |
| 6,423,057 B1 | 7/2002 | He et al. | | 6,740,079 B1 | 5/2004 | Eggers |
| 6,426,886 B1 | 7/2002 | Goder | | 6,740,085 B2 | 5/2004 | Hareyama |
| 6,428,537 B1 | 8/2002 | Swanson et al. | | 6,743,225 B2 | 6/2004 | Sanchez et al. |
| 6,436,096 B1 | 8/2002 | Hareyama | | 6,746,284 B1 | 6/2004 | Spink, Jr. |
| 6,440,157 B1 | 8/2002 | Shigezawa et al. | | 6,749,624 B2 | 6/2004 | Knowlton |
| 6,451,015 B1 | 9/2002 | Rittman, III et al. | | 6,755,825 B2 | 6/2004 | Shoenman et al. |
| 6,454,594 B2 | 9/2002 | Sawayanagi | | 6,758,846 B2 | 7/2004 | Goble et al. |
| 6,458,121 B1 | 10/2002 | Rosenstock | | 6,761,716 B2 | 7/2004 | Kadhiresan et al. |
| 6,458,122 B1 | 10/2002 | Pozzato | | 6,778,044 B2 | 8/2004 | Fehrenbach et al. |
| 6,464,689 B1 | 10/2002 | Qin | | 6,783,523 B2 | 8/2004 | Qin |
| 6,464,696 B1 | 10/2002 | Oyama | | 6,784,405 B2 | 8/2004 | Flugstad et al. |
| 6,468,270 B1 | 10/2002 | Hovda et al. | | 6,786,905 B2 | 9/2004 | Swanson et al. |
| 6,468,273 B1 | 10/2002 | Leveen et al. | | 6,790,206 B2 | 9/2004 | Panescu |
| 6,482,201 B1 | 11/2002 | Olsen et al. | | 6,792,390 B1 | 9/2004 | Burnside et al. |
| 6,488,678 B2 | 12/2002 | Sherman | | 6,796,980 B2 | 9/2004 | Hall |
| 6,494,880 B1 | 12/2002 | Swanson et al. | | 6,796,981 B2 | 9/2004 | Wham |
| 6,497,659 B1 | 12/2002 | Rafert | | 6,809,508 B2 | 10/2004 | Donofrio |
| 6,498,466 B1 | 12/2002 | Edwards | | 6,818,000 B2 | 11/2004 | Muller et al. |
| 6,506,189 B1 | 1/2003 | Rittman, III et al. | | 6,824,539 B2 | 11/2004 | Novak |
| 6,508,815 B1 | 1/2003 | Strul | | 6,830,569 B2 | 12/2004 | Thompson |
| 6,511,476 B2 | 1/2003 | Hareyama | | 6,837,888 B2 | 1/2005 | Ciarrocca et al. |
| 6,511,478 B1 | 1/2003 | Burnside | | 6,843,682 B2 | 1/2005 | Matsuda et al. |
| 6,517,538 B1 * | 2/2003 | Jacob et al. ..................... 606/47 | | 6,843,789 B2 | 1/2005 | Goble |
| 6,522,931 B2 | 2/2003 | Manker et al. | | 6,849,073 B2 | 2/2005 | Hoey |
| 6,524,308 B1 | 2/2003 | Muller et al. | | 6,855,141 B2 | 2/2005 | Lovewell |
| 6,537,272 B2 | 3/2003 | Christopherson et al. | | 6,855,142 B2 | 2/2005 | Harano |
| 6,544,260 B1 | 4/2003 | Markel et al. | | 6,860,881 B2 | 3/2005 | Sturm |
| 6,546,270 B1 | 4/2003 | Goldin et al. | | 6,864,686 B2 | 3/2005 | Novak |
| 6,547,786 B1 | 4/2003 | Goble | | 6,875,210 B2 | 4/2005 | Refior |
| 6,557,559 B1 | 5/2003 | Eggers et al. | | 6,890,331 B2 | 5/2005 | Kristensen |
| 6,558,376 B2 | 5/2003 | Bishop | | 6,893,435 B2 | 5/2005 | Goble |
| 6,558,377 B2 | 5/2003 | Lee et al. | | 6,899,538 B2 | 5/2005 | Matoba |
| 6,560,470 B1 | 5/2003 | Pologe | | 6,923,804 B2 | 8/2005 | Eggers et al. |
| 6,562,037 B2 | 5/2003 | Paton | | 6,929,641 B2 | 8/2005 | Goble et al. |
| 6,565,559 B2 | 5/2003 | Eggleston | | 6,936,047 B2 | 8/2005 | Nasab et al. |
| 6,565,562 B1 | 5/2003 | Shah et al. | | 6,939,344 B2 | 9/2005 | Kreindel |
| 6,575,969 B1 | 6/2003 | Rittman, III et al. | | 6,939,346 B2 | 9/2005 | Kannenberg et al. |
| 6,578,579 B2 | 6/2003 | Burnside et al. | | 6,939,347 B2 | 9/2005 | Thompson |
| 6,579,288 B1 | 6/2003 | Swanson et al. | | 6,942,660 B2 | 9/2005 | Pantera et al. |
| 6,582,427 B1 | 6/2003 | Goble et al. | | 6,948,503 B2 | 9/2005 | Refior et al. |
| 6,602,243 B2 | 8/2003 | Noda | | 6,958,064 B2 | 10/2005 | Rioux et al. |
| 6,602,252 B2 | 8/2003 | Mollenauer | | 6,962,587 B2 | 11/2005 | Johnson et al. |
| 6,611,793 B1 | 8/2003 | Burnside et al. | | 6,966,907 B2 | 11/2005 | Goble |
| 6,620,157 B1 | 9/2003 | Dabney et al. | | 6,970,752 B1 | 11/2005 | Lim et al. |
| 6,620,189 B1 | 9/2003 | Machold et al. | | 6,974,453 B2 | 12/2005 | Woloszko et al. |
| 6,623,423 B2 | 9/2003 | Sakurai et al. | | 6,974,463 B2 | 12/2005 | Magers et al. |
| 6,626,901 B1 | 9/2003 | Treat et al. | | 6,977,495 B2 | 12/2005 | Donofrio |
| 6,629,973 B1 | 10/2003 | Wardell et al. | | 6,984,231 B2 | 1/2006 | Goble et al. |
| 6,632,193 B1 | 10/2003 | Davison et al. | | 6,989,010 B2 | 1/2006 | Francischelli et al. |
| 6,635,056 B2 | 10/2003 | Kadhiresan et al. | | 6,994,704 B2 | 2/2006 | Qin et al. |
| 6,635,057 B2 | 10/2003 | Harano | | 6,994,707 B2 | 2/2006 | Ellman et al. |
| 6,645,198 B1 | 11/2003 | Bommannan et al. | | 7,001,379 B2 | 2/2006 | Behl et al. |
| 6,648,883 B2 | 11/2003 | Francischelli | | 7,001,381 B2 | 2/2006 | Harano et al. |

| Patent/Pub No. | Date | Inventor(s) |
|---|---|---|
| 7,004,174 B2 | 2/2006 | Eggers et al. |
| 7,008,369 B2 | 3/2006 | Cuppen |
| 7,008,417 B2 | 3/2006 | Eick |
| 7,008,421 B2 | 3/2006 | Daniel et al. |
| 7,025,764 B2 | 4/2006 | Paton et al. |
| 7,033,351 B2 | 4/2006 | Howell |
| 7,041,096 B2 | 5/2006 | Malis et al. |
| 7,044,948 B2 | 5/2006 | Keppel |
| 7,044,949 B2 | 5/2006 | Orszulak et al. |
| 7,060,063 B2 | 6/2006 | Marion et al. |
| 7,062,331 B2 | 6/2006 | Zarinetchi et al. |
| 7,063,692 B2 | 6/2006 | Sakurai et al. |
| 7,066,933 B2 | 6/2006 | Hagg |
| 7,074,217 B2 | 7/2006 | Strul et al. |
| 7,083,618 B2 | 8/2006 | Couture et al. |
| 7,094,231 B1 | 8/2006 | Ellman et al. |
| 7,104,834 B2 | 9/2006 | Robinson et al. |
| RE39,358 E | 10/2006 | Goble |
| 7,115,121 B2 | 10/2006 | Novak |
| 7,115,124 B1 | 10/2006 | Xiao |
| 7,118,564 B2 | 10/2006 | Ritchie et al. |
| 7,122,031 B2 | 10/2006 | Edwards et al. |
| 7,131,445 B2 | 11/2006 | Amoah |
| 7,131,860 B2 | 11/2006 | Sartor et al. |
| 7,137,980 B2 | 11/2006 | Buysse et al. |
| 7,146,210 B2 | 12/2006 | Palti |
| 7,147,638 B2 | 12/2006 | Chapman et al. |
| 7,151,964 B2 | 12/2006 | Desai et al. |
| 7,153,300 B2 | 12/2006 | Goble |
| 7,156,842 B2 | 1/2007 | Sartor et al. |
| 7,156,844 B2 | 1/2007 | Reschke et al. |
| 7,156,846 B2 | 1/2007 | Dycus et al. |
| 7,160,293 B2 | 1/2007 | Sturm et al. |
| 7,163,536 B2 | 1/2007 | Godara |
| 7,166,986 B2 | 1/2007 | Kendall |
| 7,169,144 B2 | 1/2007 | Hoey et al. |
| 7,172,591 B2 | 2/2007 | Harano et al. |
| 7,175,618 B2 | 2/2007 | Dabney et al. |
| 7,175,621 B2 | 2/2007 | Heim et al. |
| 7,192,427 B2 | 3/2007 | Chapelon et al. |
| 7,195,627 B2 | 3/2007 | Amoah et al. |
| 7,200,010 B2 | 4/2007 | Broman et al. |
| 7,203,556 B2 | 4/2007 | Daners |
| 7,211,081 B2 | 5/2007 | Goble |
| 7,214,224 B2 | 5/2007 | Goble |
| 7,217,269 B2 | 5/2007 | El-Galley et al. |
| 7,220,260 B2 | 5/2007 | Fleming et al. |
| 7,223,264 B2 | 5/2007 | Daniel et al. |
| 7,226,447 B2 | 6/2007 | Uchida et al. |
| 7,229,469 B1 | 6/2007 | Witzel et al. |
| 7,232,437 B2 | 6/2007 | Berman et al. |
| 7,238,181 B2 | 7/2007 | Daners et al. |
| 7,238,183 B2 | 7/2007 | Kreindel |
| 7,244,255 B2 | 7/2007 | Daners et al. |
| 7,247,155 B2 | 7/2007 | Hoey et al. |
| 7,250,048 B2 | 7/2007 | Francischelli et al. |
| 7,250,746 B2 | 7/2007 | Oswald et al. |
| 7,255,694 B2 | 8/2007 | Keppel |
| 7,258,688 B1 | 8/2007 | Shah et al. |
| 7,282,048 B2 | 10/2007 | Goble et al. |
| 7,282,049 B2 | 10/2007 | Orszulak et al. |
| 7,285,117 B2 | 10/2007 | Krueger et al. |
| 7,294,127 B2 | 11/2007 | Leung et al. |
| 7,300,435 B2 | 11/2007 | Wham et al. |
| 7,300,437 B2 | 11/2007 | Pozzato |
| 7,303,557 B2 | 12/2007 | Wham et al. |
| 7,305,311 B2 | 12/2007 | Van Zyl |
| 7,317,954 B2 | 1/2008 | McGreevy |
| 7,317,955 B2 | 1/2008 | McGreevy |
| 7,324,357 B2 | 1/2008 | Miura et al. |
| 7,333,859 B2 | 2/2008 | Rinaldi et al. |
| 7,341,586 B2 | 3/2008 | Daniel et al. |
| 7,344,532 B2 | 3/2008 | Goble et al. |
| 7,353,068 B2 | 4/2008 | Tanaka et al. |
| 7,354,436 B2 | 4/2008 | Rioux et al. |
| 7,357,800 B2 | 4/2008 | Swanson |
| 7,364,577 B2 | 4/2008 | Wham et al. |
| 7,364,578 B2 | 4/2008 | Francischelli et al. |
| 7,364,972 B2 | 4/2008 | Ono et al. |
| 7,367,972 B2 | 5/2008 | Francischelli et al. |
| RE40,388 E | 6/2008 | Gines |
| 7,396,336 B2 | 7/2008 | Orszulak et al. |
| 7,402,754 B2 | 7/2008 | Kirwan, Jr. et al. |
| D574,323 S | 8/2008 | Waaler |
| 7,407,502 B2 | 8/2008 | Strul et al. |
| 7,416,437 B2 | 8/2008 | Sartor et al. |
| 7,416,549 B2 | 8/2008 | Young et al. |
| 7,422,582 B2 | 9/2008 | Malackowski et al. |
| 7,422,586 B2 | 9/2008 | Morris et al. |
| 7,425,835 B2 | 9/2008 | Eisele |
| 7,465,302 B2 | 12/2008 | Odell et al. |
| 7,470,272 B2 | 12/2008 | Mulier et al. |
| 7,477,080 B1 | 1/2009 | Fest |
| 7,479,140 B2 | 1/2009 | Ellman et al. |
| 7,491,199 B2 | 2/2009 | Goble |
| 7,491,201 B2 | 2/2009 | Shields et al. |
| 7,503,917 B2 | 3/2009 | Sartor et al. |
| 7,513,896 B2 | 4/2009 | Orszulak |
| 7,517,351 B2 | 4/2009 | Culp et al. |
| 7,525,398 B2 | 4/2009 | Nishimura et al. |
| 7,582,084 B2 | 9/2009 | Swanson et al. |
| 2002/0029036 A1 | 3/2002 | Goble et al. |
| 2003/0181898 A1 | 9/2003 | Bowers |
| 2004/0015159 A1 | 1/2004 | Slater et al. |
| 2004/0030330 A1 | 2/2004 | Brassell et al. |
| 2004/0068304 A1 | 4/2004 | Paton |
| 2004/0097912 A1 | 5/2004 | Gonnering |
| 2004/0143263 A1 | 7/2004 | Schechter et al. |
| 2004/0172016 A1 | 9/2004 | Bek et al. |
| 2005/0004564 A1 | 1/2005 | Wham |
| 2005/0004634 A1 | 1/2005 | Ricart et al. |
| 2005/0021020 A1 | 1/2005 | Blaha et al. |
| 2005/0109111 A1 | 5/2005 | Manlove et al. |
| 2005/0113823 A1* | 5/2005 | Reschke et al. .................. 606/42 |
| 2005/0182398 A1 | 8/2005 | Paterson |
| 2005/0197659 A1 | 9/2005 | Bahney |
| 2005/0203504 A1 | 9/2005 | Wham et al. |
| 2006/0015095 A1 | 1/2006 | Desinger et al. |
| 2006/0025760 A1 | 2/2006 | Podhajsky |
| 2006/0079871 A1 | 4/2006 | Plaven et al. |
| 2006/0111711 A1 | 5/2006 | Goble |
| 2006/0161148 A1 | 7/2006 | Behnke |
| 2006/0178664 A1 | 8/2006 | Keppel |
| 2006/0224152 A1 | 10/2006 | Behnke et al. |
| 2006/0291178 A1 | 12/2006 | Shih |
| 2006/0293649 A1 | 12/2006 | Lorang et al. |
| 2007/0038209 A1 | 2/2007 | Buysse et al. |
| 2007/0088413 A1 | 4/2007 | Weber et al. |
| 2007/0093800 A1 | 4/2007 | Wham et al. |
| 2007/0093801 A1 | 4/2007 | Behnke |
| 2007/0135812 A1 | 6/2007 | Sartor |
| 2007/0173802 A1 | 7/2007 | Keppel |
| 2007/0173803 A1 | 7/2007 | Wham et al. |
| 2007/0173804 A1 | 7/2007 | Wham et al. |
| 2007/0173805 A1 | 7/2007 | Weinberg et al. |
| 2007/0173806 A1 | 7/2007 | Orszulak et al. |
| 2007/0173810 A1 | 7/2007 | Orszulak |
| 2007/0173813 A1 | 7/2007 | Odom |
| 2007/0203481 A1 | 8/2007 | Gregg et al. |
| 2007/0208339 A1 | 9/2007 | Arts et al. |
| 2007/0225698 A1 | 9/2007 | Orszulak et al. |
| 2007/0250052 A1 | 10/2007 | Wham |
| 2007/0265612 A1 | 11/2007 | Behnke et al. |
| 2007/0282320 A1 | 12/2007 | Buysse et al. |
| 2008/0015563 A1 | 1/2008 | Hoey et al. |
| 2008/0015564 A1 | 1/2008 | Wham et al. |
| 2008/0039831 A1 | 2/2008 | Odom et al. |
| 2008/0039836 A1 | 2/2008 | Odom et al. |
| 2008/0082094 A1 | 4/2008 | McPherson et al. |
| 2008/0082096 A1 | 4/2008 | Shores et al. |
| 2008/0125767 A1 | 5/2008 | Blaha |
| 2008/0177199 A1 | 7/2008 | Podhajsky |
| 2008/0248685 A1 | 10/2008 | Sartor et al. |
| 2008/0281315 A1 | 11/2008 | Gines |
| 2008/0281316 A1 | 11/2008 | Carlton et al. |
| 2008/0287791 A1 | 11/2008 | Orszulak et al. |
| 2008/0287838 A1 | 11/2008 | Orszulak et al. |
| 2009/0018536 A1 | 1/2009 | Behnke |

| | | |
|---|---|---|
| 2009/0024120 A1 | 1/2009 | Sartor |
| 2009/0036883 A1 | 2/2009 | Behnke |
| 2009/0069801 A1 | 3/2009 | Jensen et al. |
| 2009/0082765 A1 | 3/2009 | Collins et al. |
| 2009/0157071 A1 | 6/2009 | Wham et al. |
| 2009/0157072 A1 | 6/2009 | Wham et al. |
| 2009/0157073 A1 | 6/2009 | Orszulak |
| 2009/0157075 A1 | 6/2009 | Wham et al. |
| 2009/0234350 A1 | 9/2009 | Behnke et al. |
| 2009/0237169 A1 | 9/2009 | Orszulak |
| 2009/0248003 A1 | 10/2009 | Orszulak |
| 2009/0259224 A1 | 10/2009 | Wham et al. |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4206433 | 9/1993 |
| DE | 4339049 | 5/1995 |
| DE | 19506363 | 8/1996 |
| DE | 19717411 | 11/1998 |
| DE | 19848540 | 5/2000 |
| EP | 246350 | 11/1987 |
| EP | 267403 | 5/1988 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 569130 | 11/1993 |
| EP | 608609 | 8/1994 |
| EP | 694291 | 1/1996 |
| EP | 836868 | 4/1998 |
| EP | 878169 | 11/1998 |
| EP | 882955 | 12/1998 |
| EP | 1051948 | 11/2000 |
| EP | 1053720 | 11/2000 |
| EP | 1151725 | 11/2001 |
| EP | 1278007 | 1/2003 |
| EP | 1293171 | 3/2003 |
| EP | 1472984 | 11/2004 |
| EP | 1495712 | 1/2005 |
| EP | 1500378 | 1/2005 |
| EP | 1535581 | 6/2005 |
| EP | 1609430 | 12/2005 |
| EP | 1366724 | 1/2006 |
| EP | 1707144 | 3/2006 |
| EP | 1645235 | 4/2006 |
| EP | 880220 | 6/2006 |
| EP | 1681026 | 7/2006 |
| EP | 1707143 | 10/2006 |
| EP | 1744354 | 1/2007 |
| EP | 1810628 | 7/2007 |
| EP | 1810630 | 7/2007 |
| EP | 1810633 | 7/2007 |
| EP | 1854423 | 11/2007 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| GB | 607850 | 9/1948 |
| GB | 702510 | 1/1954 |
| GB | 855459 | 11/1960 |
| GB | 902775 | 8/1962 |
| GB | 2154881 | 9/1985 |
| GB | 2164473 | 3/1986 |
| GB | 2214430 | 9/1989 |
| GB | 2331247 | 5/1999 |
| GB | 2358934 | 8/2001 |
| SU | 166452 | 1/1965 |
| SU | 727201 | 4/1980 |
| WO | WO92/06642 | 4/1992 |
| WO | WO93/24066 | 12/1993 |
| WO | WO94/24949 | 11/1994 |
| WO | WO94/28809 | 12/1994 |
| WO | WO95/09577 | 4/1995 |
| WO | WO95/19148 | 7/1995 |
| WO | WO95/25471 | 9/1995 |
| WO | WO95/25472 | 9/1995 |
| WO | WO96/02180 | 2/1996 |
| WO | WO96/04860 | 2/1996 |
| WO | WO96/08794 | 3/1996 |
| WO | WO96/18349 | 6/1996 |
| WO | WO96/29946 | 10/1996 |
| WO | WO96/39086 | 12/1996 |
| WO | WO96/39088 | 12/1996 |
| WO | WO96/39914 | 12/1996 |
| WO | WO97/06739 | 2/1997 |
| WO | WO97/06740 | 2/1997 |
| WO | WO97/06855 | 2/1997 |
| WO | WO97/11648 | 4/1997 |
| WO | WO97/17029 | 5/1997 |
| WO | WO98/07378 | 2/1998 |
| WO | WO98/18395 | 5/1998 |
| WO | WO98/27880 | 7/1998 |
| WO | WO99/12607 | 3/1999 |
| WO | WO99/56647 | 11/1999 |
| WO | WO01/01847 | 1/2001 |
| WO | WO02/00129 | 1/2002 |
| WO | WO02/11634 | 2/2002 |
| WO | WO02/45589 | 6/2002 |
| WO | WO02/47565 | 6/2002 |
| WO | WO02/053048 | 7/2002 |
| WO | WO02/088128 | 7/2002 |
| WO | WO03/090630 | 11/2003 |
| WO | WO03/090635 | 11/2003 |
| WO | WO03/092520 | 11/2003 |
| WO | WO2004/028385 | 4/2004 |
| WO | WO2004/098385 | 4/2004 |
| WO | WO2004/043240 | 5/2004 |
| WO | WO2004/052182 | 6/2004 |
| WO | WO2004/103156 | 12/2004 |
| WO | WO2005/046496 | 5/2005 |
| WO | WO2005/048809 | 6/2005 |
| WO | WO2005/050151 | 6/2005 |
| WO | WO2005/060365 | 7/2005 |
| WO | WO2005/060849 | 7/2005 |
| WO | WO2006/050888 | 5/2006 |
| WO | WO2006/105121 | 10/2006 |

OTHER PUBLICATIONS

U.S. Appl. No. 10/573,713, filed Mar. 28, 2006.
U.S. Appl. No. 11/242,458, filed Oct. 3, 2005.
U.S. Appl. No. 12/136,620, filed Jun. 10, 2008.
U.S. Appl. No. 12/184,556, filed Aug. 1, 2008.
U.S. Appl. No. 12/203,734, filed Sep. 3, 2008.
U.S. Appl. No. 12/205,298, filed Sep. 5, 2008.
U.S. Appl. No. 12/205,525, filed Sep. 5, 2008.
U.S. Appl. No. 12/241,861, filed Sep. 30, 2008.
U.S. Appl. No. 12/241,905, filed Sep. 30, 2008.
U.S. Appl. No. 12/241,942, filed Sep. 30, 2008.
U.S. Appl. No. 12/241,983, filed Sep. 30, 2008.
U.S. Appl. No. 12/242,026, filed Sep. 30, 2008.
U.S. Appl. No. 12/242,061, filed Sep. 30, 2008.

U.S. Appl. No. 12/242,102, filed Sep. 30, 2008.
U.S. Appl. No. 12/249,218, filed Oct. 10, 2008.
U.S. Appl. No. 12/249,263, filed Oct. 10, 2008.
U.S. Appl. No. 12/351,935, filed Jan. 12, 2009.
U.S. Appl. No. 12/351,947, filed Jan. 12, 2009.
U.S. Appl. No. 12/351,960, filed Jan. 12, 2009.
U.S. Appl. No. 12/351,970, filed Jan. 12, 2009.
U.S. Appl. No. 12/351,980, filed Jan. 12, 2009.
U.S. Appl. No. 12/353,002, filed Jan. 13, 2009.
U.S. Appl. No. 12/353,012, filed Jan. 13, 2009.
U.S. Appl. No. 12/407,896, filed Mar. 20, 2009.
U.S. Appl. No. 12/477,245, filed Jun. 3, 2009.
U.S. Appl. No. 12/481,087, filed Jun. 9, 2009.
U.S. Appl. No. 12/534,308, filed Aug. 3, 2009.
U.S. Appl. No. 12/540,190, filed Aug. 12, 2009.
U.S. Appl. No. 12/549,563, filed Aug. 28, 2009.
U.S. Appl. No. 12/556,770, filed Sep. 10, 2009.
U.S. Appl. No. 12/566,173, filed Sep. 24, 2009.
U.S. Appl. No. 12/566,233, filed Sep. 24, 2009.
U.S. Appl. No. 12/567,966, filed Sep. 28, 2009.
U.S. Appl. No. 12/613,876, filed Nov. 6, 2009.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Burdette et al. "In Vivo Probe Measurement Technique For Determining Dielectric Properties At VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedance" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight And Absorbance Imaging Of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al, "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report EP09003678.1 dated Aug. 7, 2009.
International Search Report EP09005160.8 dated Aug. 27, 2009.
International Search Report EP09009860 dated Dec. 8, 2009.
International Search Report EP09164754.5 dated Aug. 21, 2009.
International Search Report EP09169377.0 dated Dec. 15, 2009.
International Search Report EP09172749.5 dated Dec. 4, 2009.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US08/052460 dated Apr. 24, 2008.
International Search Report PCT/US09/46870 dated Jul. 21, 2009.
US 6,878,148, 04/2005, Goble et al. (withdrawn)

* cited by examiner

_US 7,972,332 B2_

SYSTEM AND METHOD FOR CONTROLLING ELECTROSURGICAL SNARES

CROSS-REFERENCE TO RELATED APPLICATION

The present application is a continuation of U.S. patent application Ser. No. 11/367,723 entitled "SYSTEM AND METHOD FOR CONTROLLING ELECTROSURGICAL SNARES" filed on Mar. 3, 2006 by Gene H. Arts et al., now U.S. Pat. No. 7,651,493, the entire contents of which are hereby incorporated be reference herein.

TECHNICAL FIELD

The present disclosure relates generally to an electrosurgical snare instrument and, more particularly, to a system and method for controlling energy delivered by an electrosurgical generator to the electrosurgical snare instrument based on diameter and pressure of the snare.

BACKGROUND OF RELATED ART

Snare instruments are electrosurgical devices that are primarily used for removing small growths from the lining of internal body cavities (e.g., polyps within the bowels), such as during polypectomy procedures. These snares include a wire loop configured to encircle the small growth, and then electrosurgical energy is applied to the tissue to cut and/or coagulate. Generally, snare instruments include an elongate tubular member having a handle, such as a sheath, a shaft extending through the tubular member having a wire loop connected to the distal end ("distal" refers to that portion that is further from the user, while "proximal" refers to that portion that is closer to the user or surgeon) thereof. The loop is opened by pushing the shaft toward the distal end thereby moving/extracting the loop outside the tubular member and is closed by pulling the shaft toward the proximal end thereby moving/retracting the loop inside the tubular member.

The snare instrument is generally inserted into internal body cavities through an endoscope. In the case of a polypectomy, the instrument is inserted through the gastrointestinal tract and moved toward the polyp(s) marked for removal. During insertion, the loop is retracted into the shaft, and once at the removal site, it is extracted and is expanded around the polyp. The surgeon then constricts the loop around the polyp and electrosurgical energy is applied thereto.

Currently, snare instruments are used without providing any sensory feedback to the generator. The surgeon has to manually adjust the energy delivered to the snare while simultaneously adjusting the pressure exacted on the polyp by the loop. For instance, as the surgeon increases the pressure, the energy must also increase so that the energy increases proportionally with pressure. The contiguous increase in pressure and energy allows for the polyp to be removed only after the stalk portion thereof has been cauterized. Increasing energy too slowly may detrimentally affect removal of the polyp causing bleeding. Increasing energy too rapidly may result in damage to the surrounding tissue. Presently, the success of these surgical procedures depended on the experience of the surgeon to control the pressure and energy delivered to the snare instrument. Such manual control of these operating factors is not infallible.

SUMMARY

The present disclosure provides for a system and method of controlling delivery of electrosurgical energy supplied by a generator to an electrosurgical snare instrument based on the position and pressure of the snare loop. The snare instrument is configured for removal of polyps and includes a position sensor configured to determine diameter of the snare loop and a pressure sensor configured to determine the pressure exacted on the polyp. The position and pressure feedback signals are transmitted to the generator, which then automatically adjusts the power of output, mode, and other factors affecting electrosurgical energy.

According to one embodiment of the present disclosure, an electrosurgical snare instrument is disclosed. The instrument includes an elongate tubular sheath having proximal and distal ends, the sheath having a longitudinal axis defined therethrough. The instrument also includes a shaft having proximal and distal ends, the shaft extending through and axially movable relative to the sheath. A snare loop is provided at the distal end of the shaft and is configured for encircling tissue. Movement of the shaft relative to the tubular sheath changes the diameter of the exposed snare loop. A feedback sensor operatively connected to the elongated tubular sheath determines at least one condition of the snare loop.

According to another embodiment of the present disclosure, a system for controlling an electrosurgical snare instrument is disclosed. The system includes an electrosurgical instrument having an elongate tubular sheath having proximal and distal ends, the sheath having a longitudinal axis defined therethrough and a shaft having proximal and distal ends. The shaft extends through and is axially movable relative to the sheath. A snare loop is provided at the distal end of the shaft and is configured for encircling tissue. Movement of the shaft relative to the tubular sheath changes the diameter of the exposed snare loop. A feedback sensor operatively connected to the elongated tubular sheath determines at least one condition of the snare loop, and an electrosurgical generator provides electrosurgical energy to the electrosurgical snare instrument. The generator is configured to receive feedback measurements from the electrosurgical snare instrument and to adjust electrosurgical energy as a function of the measurements.

According to a further embodiment of the present disclosure, a method for controlling an electrosurgical snare instrument is disclosed. The method includes the step of inserting an electrosurgical snare instrument into a body cavity. The instrument includes an elongate tubular sheath having proximal and distal ends, the sheath having a longitudinal axis defined therethrough. The instrument also includes a shaft having proximal and distal ends, the shaft extending through and axially movable relative to the sheath. A snare loop is provided at the distal end of the shaft and is configured for encircling tissue. Movement of the shaft relative to the tubular sheath changes the diameter of the exposed snare loop. The method further includes the steps of positioning the snare loop to encircle a portion of the tissue and collecting feedback measurements through a feedback sensor operatively connected to the elongated tubular sheath for determining at least one condition of the snare loop indicative of at least one condition of the snare loop. The method further includes the steps of transmitting feedback measurements to an electrosurgical generator, which provides electrosurgical current and adjusting electrosurgical energy as a function of the feedback measurements.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Embodiments of the present disclosure are described below with reference to the accompanying drawings. In the following description, well-known functions or constructions are not described in detail to avoid obscuring the present disclosure in unnecessary detail. As used herein, the term "distal" refers to that portion that is further from the user while the term "proximal" refers to that portion that is closer to the user or surgeon.

Figure 1:
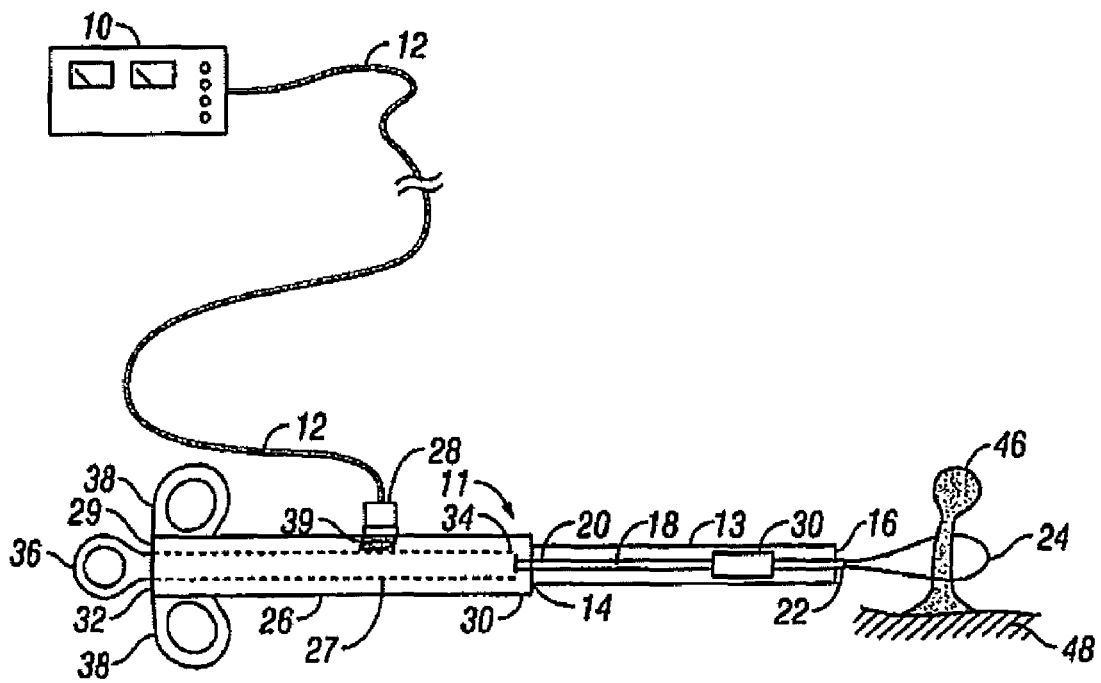
FIG. 1 is a diagram illustrating an electrosurgical system including a snare instrument according to the present disclosure.

FIG. 1 shows an electrosurgical system including a generator 10 that supplies electrosurgical energy to an electrosurgical snare instrument 11 through electrical wiring within a cable 12. The generator 10 also includes processing means (e.g., one or more microprocessors, storage, memory, etc.) configured to analyze control and input signals as discussed in more detail below. The snare instrument 11 includes an elongate tubular sheath 13 having a proximal end 14 and a distal end 16 formed preferably from a suitable medical grade plastic, such as Teflon, polyurethane, polyethylene and the like. The sheath 13 has an outside diameter sufficiently small enough to allow the sheath 13 to fit through a working lumen of an endoscope (not explicitly shown).

The snare instrument 11 also includes an electrically conductive shaft 18 having a proximal end 20 and a distal end 22 extending through and axially movable within the sheath 12. The shaft 18 may be in a form a multifilament twisted and drawn or swaged cable where the filaments are metallic, such as stainless steel, a nickel-titanium alloy, and the like. It is envisioned that the shaft 18 may be formed from a suitable plastic material, such as the plastic used to form the sheath 13, wherein the plastic includes an electrically conductive surface (e.g., coating, foil, etc.).

Figure 2:
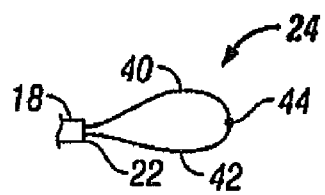
FIG. 2 is a schematic diagram illustrating a snare loop.

A snare loop 24 is mechanically and electrically coupled to the distal end 22 of shaft 18 via a connector 30 near distal end 16 of the sheath 12 as illustrated in FIG. 2. The snare loop 24 is formed from suitable wire, such as multifilament wire used to form the shaft 18. In the illustrated embodiment, the snare loop 24 includes two sides 40, 42 with corresponding two ends attached to the distal end 22 of the shaft 18 to form a loop by welding, soldering, or crimping. Alternatively, the shaft 18 may be formed from two cables to or wires twined together from the proximal end 20 and the distal end 22 and untwined after the distal end to form the loop 24. In an alternative embodiment, the two sides 40, 42 may be formed from separate wire or cable elements coupled together at the distal end 22 of the shaft 18 and the distal end 44.

The snare instrument 11 further includes a handle assembly 26 having a distal end 30 and a proximal end 29. The sheath 13 is connected to the assembly 26 at the distal end 30. The assembly 26 may have tubular structure and may be formed by molding from an inflexible plastic material or formed by other processes from other inflexible medical grade materials (e.g., stainless steel). The assembly 26 may also be formed from elastic medical grade materials (e.g., high durometer urathane).

Within the assembly 26 is a plunger 27 having a distal end 34 and a proximal end 32. The plunger 27 is electrically conductive and inflexible. The plunger 27 may be formed entirely from metal (e.g., steel rod) or from an inflexible plastic having an electrically conductive surface. The shaft 18 is connected to the plunger 27 at the shaft's proximal end 20 and plunger's distal end 34. The plunger 27 includes a first handle 36 at the proximal end 32 thereof, which allows the surgeon in conjunction with a second handle 38 disposed at the proximal end 29 of the assembly 26 to manipulate the shaft 18 and the loop 24 by moving the shaft 18 along the longitudinal axis. The second handle 38 includes finger rests adapted to receive the forefinger and index finger of the surgeon whereby the thumb is inserted into the first handle 36 to facilitate the manipulation of the plunger 27 and the shaft 18.

Disposed on the surface of the assembly 26 is a cautery connector 28 that is conductively coupled via a brush connector 39 to the shaft 18 through the plunger 27 so that the plunger 27 and the shaft 18 can be and moved longitudinally while maintaining such conductive coupling.

The snare instrument 11 can be adapted for monopolar and bipolar electrosurgical procedures. In monopolar configuration, the loop 24 serves as an active electrode through which electrosurgical energy will be applied to the tissue. In such a configuration, a return electrode (not shown) will be attached to a patient to return the current supplied through the loop 24 to the generator 10.

In bipolar configuration, the active and return electrodes are incorporated into the loop 24. One of the two sides 40, 42 serves as an active electrode while the other serves as a return electrode being separated by an insulative material (e.g., ceramic tip) at the distal end 44.

Referring back to FIG. 1, the loop 24 is shown surrounding a stalk of a polyp 46 extending outward from the surface of a hollow organ 48 in the gastrointestinal tract (e.g., bowel). During an operating procedure, the snare instrument 11 is inserted into the organ through an endoscope channel and the endoscope is used to visually locate and assess the shape and type of the polyp 46 as is well known in the art. Thereafter, the surgeon positions the snare instrument 11 within the organ and places the loop 24 around the polyp 46. Then, the surgeon retracts the loop 24 by pulling the plunger 27 toward the proximal end 32 to close the loop 24 around the polyp 46. Once the loop 24 is closed and in contact around polyp 46, the surgeon applies the coagulation current to desiccate the cells of the polyp 46, thereby severing the growth. After the severing, the surgeon switches the generator 10 into coagulating mode and places the closed loop 24 in contact with severed blood vessels of the polyp 46 to close the vessels and stop the blood flow. It is known that the loop 24 in a closed configuration may also be used to remove polyps too small to be encircled by the loop 24. Those skilled in the art will appreciate that the surgeon may also use coagulating current initially to coagulate the blood vessels within the polyp 46 and then use the cutting current to cut across or proximate the coagulated portion.

Figure 3:
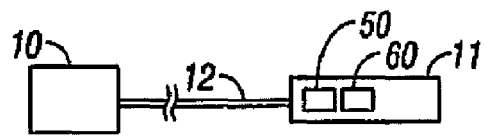
FIG. 3 is a block diagram of the electrosurgical system of FIG. 1.

To aid the surgeon in adjustment of various parameters (e.g., intensity, waveform, etc.) of the electrosurgical energy, the present disclosure provides a position sensor 50 and a pressure sensor 60 disposed within the snare instrument 11, as shown in FIG. 3, which provide feedback to the generator 10 upon which the generator 10 makes adjustment to operating parameters, such as power output, power versus impedance curves, operating mode, duty cycle, etc. The pressure sensor 60 senses the pressure exerted by the loop 24 on the polyp 46. The position sensor 50 senses the diameter of the loop 24 (i.e., perimeter and/or size of the loop 24) and reports the measurements to the generator 10, which then makes a determination based on the measurements and makes corresponding adjustments to electrosurgical energy.

More particularly, when the loop 24 is not fully closed but in contact with the polyp 46 the position sensor 50 and the pressure sensor 60 report that fact to the generator 10, which then communicates electrosurgical energy through the loop 24 so that the polyp 46 can be severed. When the loop 24 is fully closed, e.g., the polyp 46 has been fully severed, that information is forwarded by the sensors 50, 60 to the generator 10, which then switches into coagulation mode to coagulate the blood vessels. Those skilled in the art will appreciate that the generator 10 may be programmed to respond in different ways than those discussed above (e.g., coagulate when loop 24 is in contact with tissue and cut when the loop 24 is closed). The snare instrument 11 may include either one of, or both, the position sensor 50 and the pressure sensor 60 allowing the generator 10 to make power and other adjustments based on diameter and/or pressure measurements.

Figure 4:
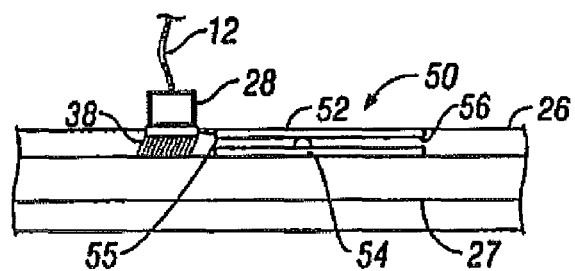
FIG. 4 is a cross sectional view of the snare instrument including a position sensor.
Figure 4A:
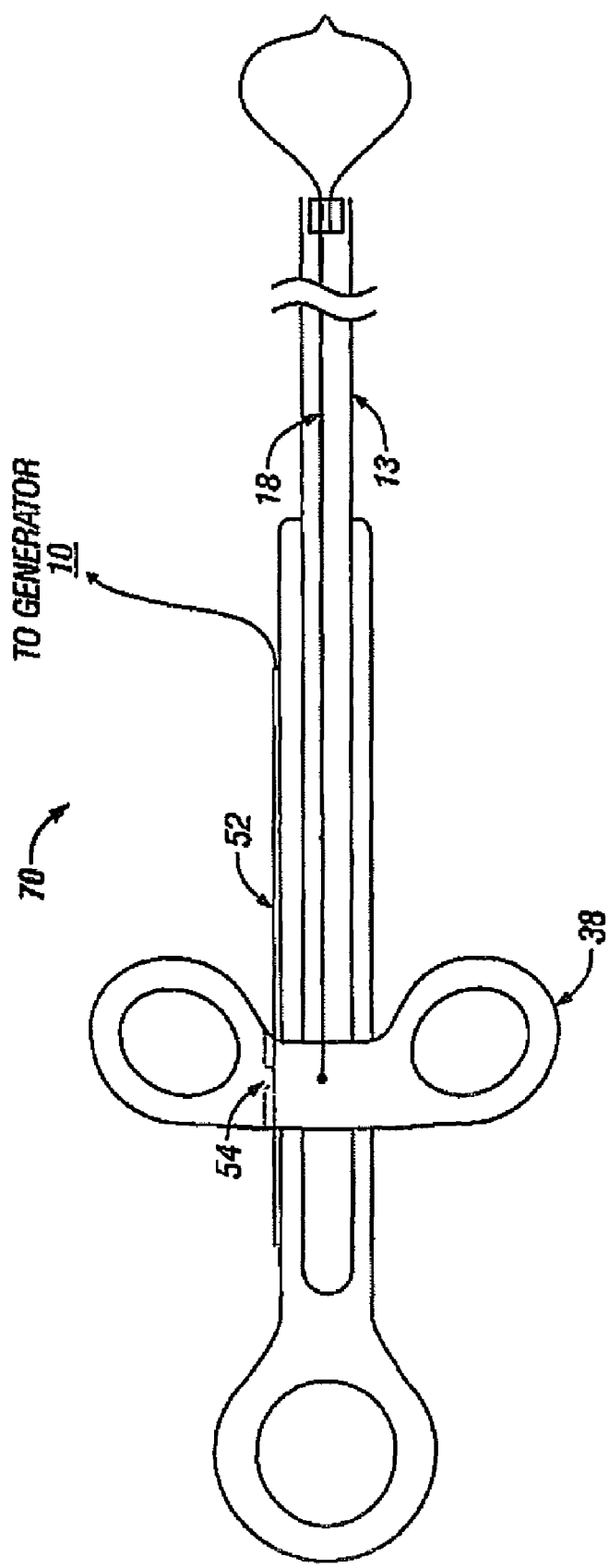
FIG. 4A is a cross sectional view of an alternate snare instrument.

With reference to FIG. 4, the position sensor 50 is shown disposed within the assembly 26. In one embodiment, the position sensor 50 includes a film-type potentiometer 52 coupled to the inner surface of the tubular structure of the assembly 26 and a contact nub 54 in contact therewith. The nub 54 is positioned on the outer surface of the plunger 27 directly opposite the potentiometer 52. The potentiometer 52 and the nub 54 may be relocated (e.g., their positions reversed) as long as these components of the position sensor 50 are kept in contact with and are positioned opposite each other. Furthermore, the potentiometer 52 may be disposed on the inner surface of the sheath 13 with the nub 54 being located on the shaft 18. The nub 54 may also be disposed (e.g., embedded) within the second handle 38 and the potentiometer 52 may be placed on the outer surface of sheath 13, as shown in FIG. 4A.

The spring sensor 60 may be constructed in the following manner. The sheath 13 and other components of the snare instrument 70 may be made from elastic materials and thereby be used to spring-load the loop 24. The spring-loading produces a signal from the position sensor 50 embedded in the second handle 38 and measures both the snare size of the loop 24 and the pressure exerted thereby.

Figure 4B:
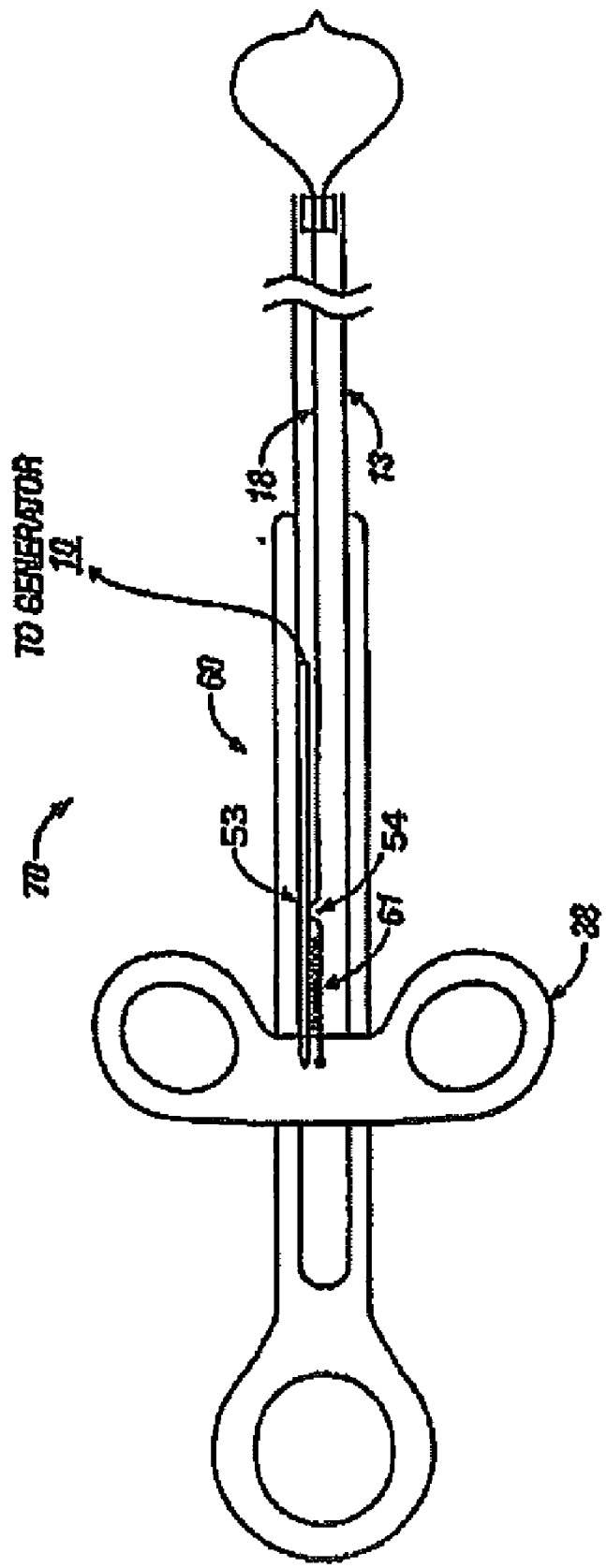
FIG. 4B is a cross sectional view of an alternate snare instrument.

With reference to FIG. 4B, a pressure sensor 60 is shown that includes the nub 55 disposed within the sheath 13 and in contact with a second potentiometer 53. The nub 55 is coupled to the second handle 38 through a suitable elastic member 61 (e.g., a spring) connected in series thereto. The position of the nub 54 and its contact with the potentiometer 53 is directly proportional to the force with which the second handle 38 is pushed pack (e.g., counterbalanced by the elastic member 61). Therefore, the pressure exerted by loop 24 may be determined by measuring the signal generated by the nub 54 contacting the potentiometer 53. The pressure sensor 60 may also be a piezoelectric crystal. The piezoelectric crystal converts pressure applied thereto into corresponding voltage that can then be converted into a digital signal and be processed by the processing means of the generator 10.

Figure 4C:
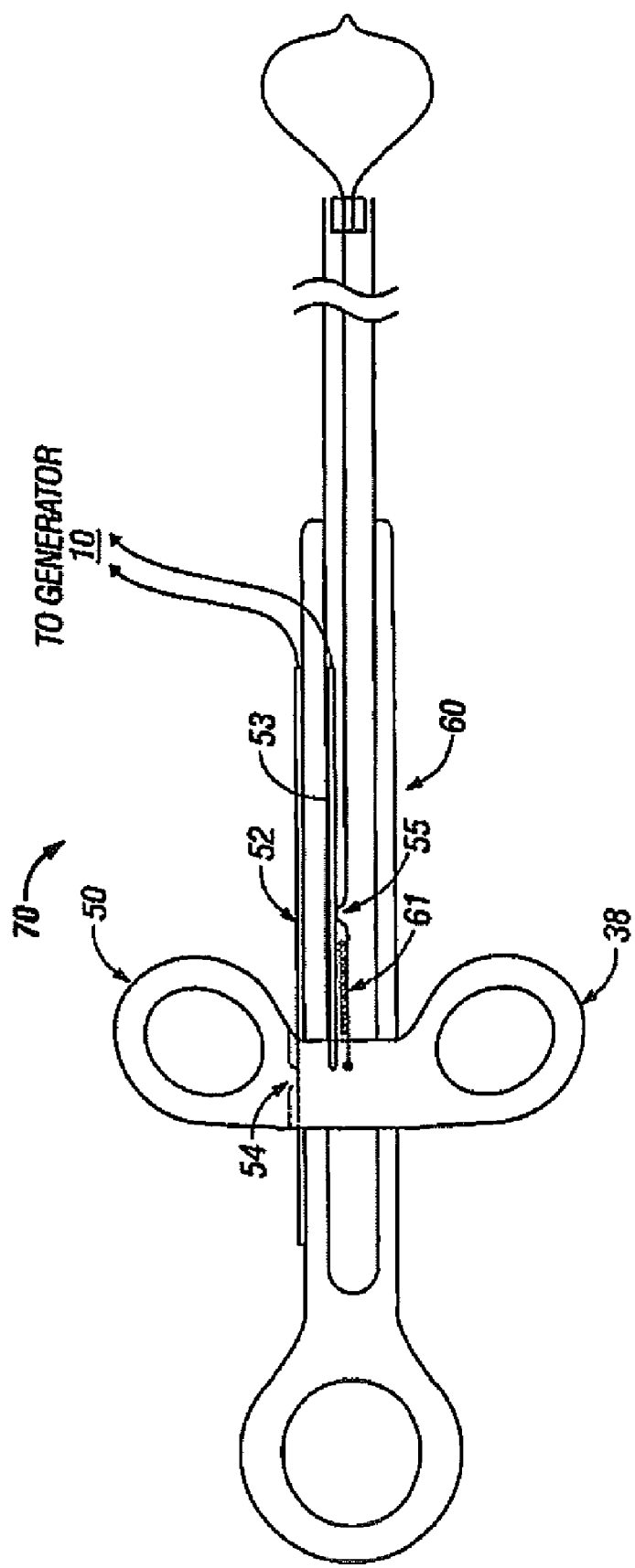
FIG. 4C is a cross sectional view of an alternate snare instrument.

As shown in FIG. 4C, the pressure and position sensors 50, 60 are disposed within the snare instrument 70. The position sensor 50 measures the diameter of the loop 24 using the position of the nub 54 and the pressure sensor 60 measures the pressure exerted by the loop 24 by determining the position of the nub 54 as affected by the elastic member 61.

The feedback concerning the diameter of the loop 24 is reported to the generator 10 through control wires disposed within the cable 12. As the plunger 27 is moved longitudinally within the handle assembly 26, the nub 54 slides longitudinally across the surface of the potentiometer 52. When the nub 54 is in contact with the potentiometer 52 near a proximal end 55 thereof, a corresponding voltage is transmitted to the generator 10. The voltage is analyzed by the generator 10 to determine the control signal, which when the nub 54 is near or at the proximal end 55, denotes that the loop 24 is in closed position (e.g., shaft 18 is fully retracted). When nub 54 is in contact with the potentiometer 52 near a distal end 56, the voltage transmitted to the generator 10 signals that the loop 24 is fully opened. Positions of the nub 54 in between the proximal and distal ends 55, 56 can be configured to denote other corresponding control signals (e.g., partially closed loop 24). After analyzing the control signals and determining the position of the loop 24, the generator 10 makes appropriate changes to the output of the electrosurgical energy, such as output power, waveform, voltage, impedance, mode, etc.

In addition to providing feedback on the position and diameter of the loop 24, the present disclosure also provides for a system and method to determine the pressure exerted by the loop 24 on the polyp 46 using the pressure sensor 60, as shown in FIG. 3. Determining the snare loop 24 pressure may be important in determining when power must be applied to the polyp 46. As discussed above, initially power is applied to the polyp, more specifically, a coagulation mode is used. Conventionally, surgeons had to figure out when to sever the polyp based on experience. The pressure sensor 60 allows for automatic adjustment by providing feedback to the generator 10 concerning the pressure applied to the polyp 46. When the pressure sensor 60 senses that the pressure is at its highest, it denotes that the loop 24 is firmly fitted around the polyp 46. This information is transmitted to the generator 10 which increases power or switches operational modes (e.g., cutting mode) and supplies electrosurgical energy to the snare instrument 11. As soon as the polyp 46 is severed, the pressure applied by the loop 24 dissipates since the physical obstruction (e.g., polyp 46) has been removed. This change in pressure is also transmitted to the generator 10 which then modifies the operating mode and supplies coagulating current to the snare instrument 11 to coagulate the blood vessels.

The pressure sensor 60 may enable the surgeon to regulate the pressure such that the surgeon can effectively seal the blood vessels prior to resection of the polyp 46. For example, the surgeon may be able to control the pressure applied around the polyp 46 to within an ideal parameter known to effectively seal tissue rather than simply coagulate tissue. Other features may also have to be properly controlled to create an effective seal, such as gap distance between opposing surfaces of the loop 24 and energy control.

Where elastic compliance of the materials comprising the components of the snare instrument 70 are known, a single position sensor may be used to sense position as well as the pressure of the snare. In particular, the position measurement signal in conjunction with the elastic properties may be used to calculate the pressure and position of the snare based on a single signal. Conventional materials used in construction of snare instruments are prone to compress and stretch when force is applied to the handle. Therefore, placing the position sensor 50 at the handle 38 allows for measuring the position and the pressure of the snare. A single pressure sensor 60 may be used to determine both the position and the pressure of the snare from the pressure signal based on the elastic compliance of the flexible snare materials.

The snare instrument 70 may include an impedance sensor (not explicitly shown) that measures impedance of the tissue at the polyp 46. Using a sensing current the impedance sensor determines when sufficient energy has been communicated to the polyp 46 to signal the polyp 46 has been coagulated and may be severed. Impedance measurements may also be used to determine when other stages of the procedure have been accomplished, since as energy is applied to the polyp 46 impedance of the tissue changes, which allows for measurements and/or determinations regarding the state of the polyp 46.

Those skilled in the art will appreciate that the generator 10 includes a specific operating mode designed for snare procedures. Snare procedures differ from other electrosurgical operations (e.g., sealing blood vessels, cutting tissue, etc.) because the electrode in snare procedures (e.g., loop 24) is in continuous tissue contact. As a result snare procedures are characterized by low impedance of the tissue and low voltage requirements. The generator 10 of the present disclosure includes a new operating mode that changes output power, waveform, and voltage relative to the tissue impedance. This operating mode may be also useful in other electrosurgical procedures having same characteristics as snare procedures where an active electrode is in continuous tissue contact.

Figure 5:
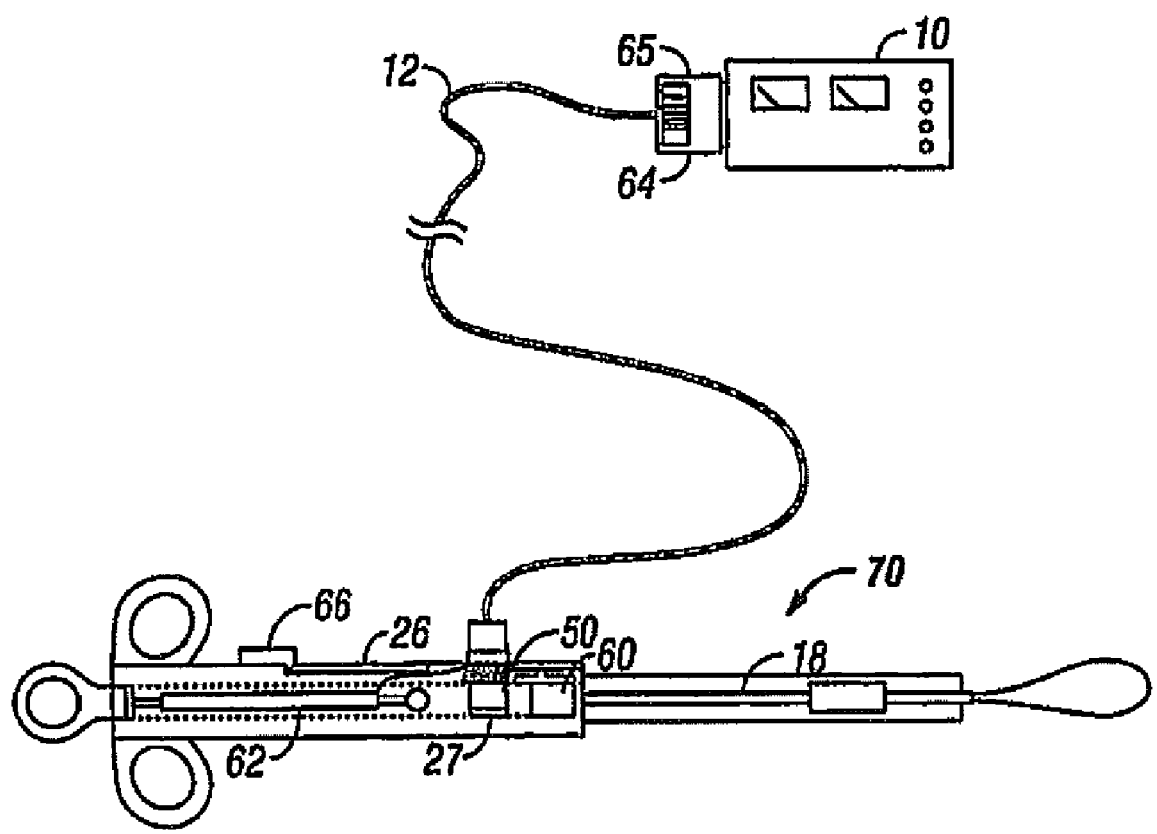
FIG. 5 is a diagram illustrating an alternate embodiment of an electrosurgical system according to the present disclosure.

Pressure and loop diameter feedback can also be used to fully automate snare procedures by using a snare instrument 70 as shown in FIG. 5. The application of electrosurgical energy as well as diameter control of the loop 24 may be controlled by the generator 10 based on the feedback received from the sensors 50, 60. The snare instrument 70 includes an actuator 62, such as a piston cylinder which is electrically controlled by the generator 10 or a cable controller actuated by a pulley system. An algorithm for controlling the actuator 62 is programmed in the generator 10 and may be activated by scanning a barcode 64 attached to a plug 65. It is well known in the art to identify devices by scanning barcodes and loading preprogrammed algorithms into the electrosurgical generators based on that information. The generator 10 may include a reader for scanning barcodes and other identifying means.

The snare instrument 70 also includes a button 66 that activates the snare instrument 70 once it is in position (e.g., the loop 24 is placed around the polyp 46). Once the proper positioning is achieved, the surgeon presses the button 66 to activate the generator 10 algorithm. The generator 10 adjusts the diameter of the loop 24 by decreasing the diameter gradually. More particularly, the generator 10 signals the actuator 62 to contract, thereby pulling the shaft 18 and contracting the loop 24. The contraction continues until the pressure sensor 60 reports to the generator 10 that the loop 24 is in tight contact with the polyp 46. The generator 10 then checks the tissue impedance and delivers electrosurgical energy of predefined operating made and power level to the loop 24 based on pressure feedback and measured impedance. Impedance measurement may be carried out by supplying a measuring current to the polyp 46 to determine is impedance as is known in the art.

Once the energy is supplied to the polyp 46 and it is severed, the position sensor 50 reports to the generator 10 of this occurrence and the generator 10 responds to the position feedback by changing operating modes (e.g., switch to coagulation mode). The mode and power settings can be changed during the procedure as a response to measured tissue impedance and loop diameter. Once the resection of the polyp 46 is complete, the energy is turned off to reduce the possibility of affecting surrounding tissue. During various stages of the procedure one or more audio and/or visual indicator may be used to signal to the surgeon that a particular stage of the procedure is completed. The audio and/or visual indicators can be disposed on the generator 10 or snare instrument 70.

Figure 6:
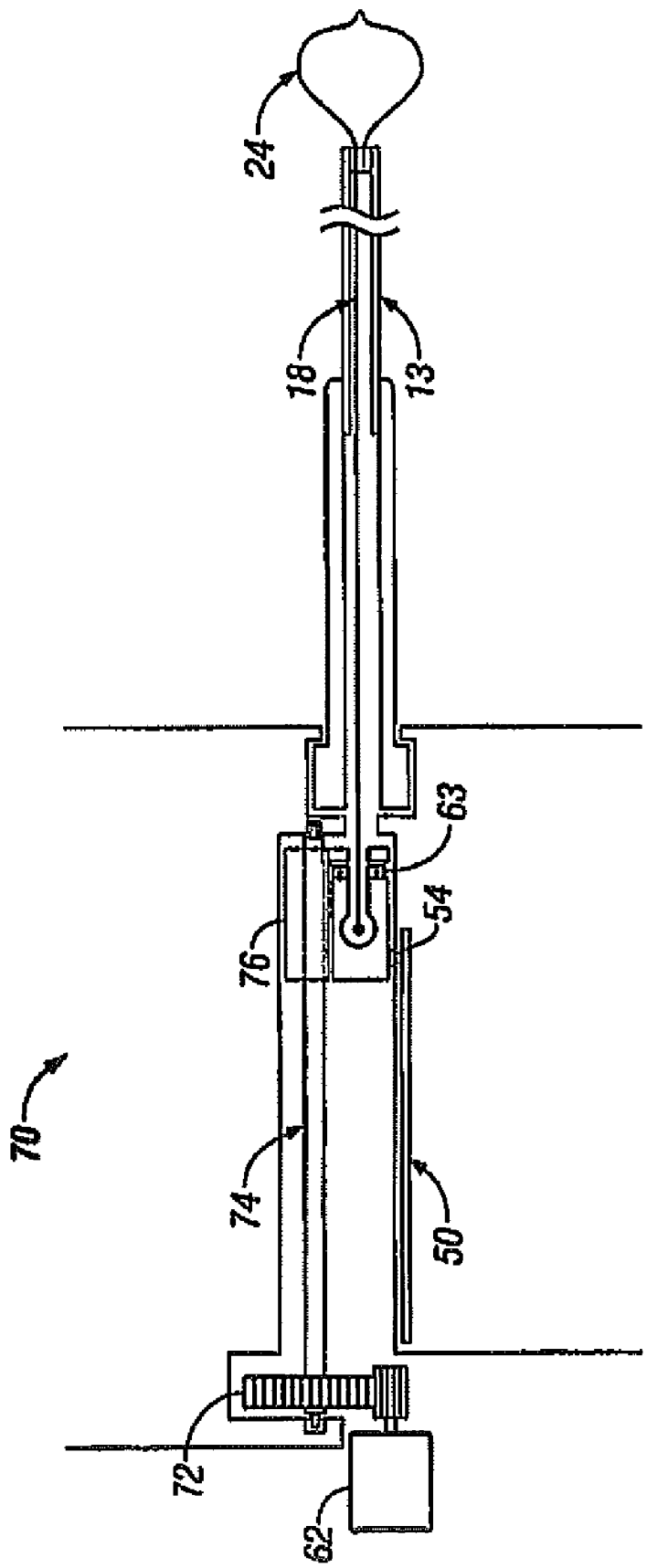
FIG. 6 is a diagram illustrating another alternate embodiment of an electrosurgical system according to the present disclosure.

FIG. 6 shows another embodiment of the snare instrument 70 that is automatically activated and monitored by the generator 10. The snare instrument 70 includes a drive motor 62 that is controlled by the generator 10. The drive motor 62 actuates a gear mechanism 72 that rotates a lead screw 74, which in turn is connected to a block 76 that includes the shaft 18. The drive motor 62 may rotate the lead screw in two directions (e.g., clockwise and counterclockwise), which then moves the block 76 and the shaft 18 backwards and forwards. The block 76 includes the nub 54 that is in contact with the potentiometer 52 to measure the diameter of the loop 24. In addition, the block 76 also includes a piezoelectric crystal 63, which converts pressure applied thereto into a corresponding voltage signal. The voltage signal may then be analyzed by the processing means of the generator 10.

The generator 10 measures pressure and size of the loop 24 and includes suitable algorithms that control the drive motor 62, through which the generator 10 controls snare pressure, snare exposure (e.g., size of the loop 24), generator mode, and generator power to optimize cautery and resection procedures.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. An electrosurgical instrument comprising:
a tubular sheath having proximal and distal ends;
a snare loop coupled to the distal end of the tubular sheath, the snare loop configured to encircle tissue; and
a feedback sensor operatively coupled to the tubular sheath and configured to provide feedback to a generator, the feedback sensor including:
a position sensor configured to measure a position of the snare loop, the position sensor including a potentiometer; and
a pressure sensor configured to measure pressure exerted by the snare loop on the encircled tissue.

2. The electrosurgical instrument according to claim 1, wherein the tubular sheath is an elongated flexible tubular sheath having a longitudinal axis defined therethrough.

3. The electrosurgical instrument according to claim 1, further comprising a shaft having proximal and distal ends, the shaft extending through and axially moveable relative to the sheath.

4. The electrosurgical instrument according to claim 3, wherein the snare loop is coupled at the distal end of the shaft such that the movement of the shaft relative to the tubular sheath adjusts a diameter of the snare loop.

5. The electrosurgical instrument according to claim 3, further comprising a nub disposed on the shaft, wherein the potentiometer is disposed on an inner surface of the sheath and is at least in partial contact with the nub.

6. The electrosurgical instrument according to claim 1, wherein the pressure sensor includes a piezoelectric crystal.

7. The electrosurgical instrument according to claim 1, wherein the feedback sensor determines whether the snare loop is fully retracted and the tissue is severed.

8. The electrosurgical instrument according to claim 1, wherein the generator is an electrosurgical generator configured to provide electrosurgical energy to the electrosurgical instrument, the generator configured to receive feedback from the feedback sensors and to adjust electrosurgical energy as a function of the feedback.

9. The electrosurgical instrument according to claim 8, wherein the generator automatically controls the movement of a shaft and diameter of the snare loop.

10. The electrosurgical instrument according to claim 8, further including identifying means readable by the generator, the identifying means comprising instructions to configure the generator.

11. A method for performing electrosurgical procedures, the method comprising the steps of
inserting an electrosurgical instrument into a body cavity, the instrument including:
a tubular sheath having proximal and distal ends; and
a snare loop disposed at the distal end of the tubular sheath;
positioning the snare loop to encircle a portion of the tissue;
collecting feedback indicative of at least one condition of the snare loop through a feedback sensor operatively coupled to the tubular sheath;
transmitting the feedback to an electrosurgical generator that provides electrosurgical energy; and
adjusting electrosurgical energy and the diameter of the snare loop as a function of the feedback.

12. The method according to claim 11, wherein the tubular sheath is an elongated flexible tubular sheath having a longitudinal axis defined therethrough.

13. The method according to claim 11, wherein the instrument further includes a shaft having proximal and distal ends, the shaft extending through and axially moveable relative to the sheath.

14. The method according to claim 13, wherein the snare loop is coupled at the distal end of the shaft and is configured to encircle the tissue.

15. The method according to claim 14, wherein the positioning step further includes the step of moving the shaft relative to the tubular sheath to adjust a diameter of the snare loop.

16. The method according to claim 11, wherein the feedback is selected from the group consisting of snare loop diameter, pressure exerted on the snare loop and impedance.

17. The method according to claim 11, wherein the feedback sensor includes a position sensor having a potentiometer disposed on an inner surface of the sheath and a nub disposed on the shaft, the nub being at least in partial contact with the potentiometer.

18. The method according to claim 11, further comprising the step of determining whether the snare loop is fully retracted and the tissue is severed.

19. The method according to claim 11, further comprising the step of determining whether the snare loop is in contact with the tissue.

* * * * *